United States Patent
Sui et al.

[11] Patent Number: 5,995,235
[45] Date of Patent: Nov. 30, 1999

[54] BANDPASS PHOTON DETECTOR

[75] Inventors: Zhifeng Sui, Milpitas; Paul E. Luscher, Sunnyvale, both of Calif.

[73] Assignee: Applied Materials, Inc., Santa Clara, Calif.

[21] Appl. No.: 08/800,003

[22] Filed: Feb. 13, 1997

[51] Int. Cl.[6] .............................. G01J 3/51; G01N 21/25
[52] U.S. Cl. .................... 356/419; 356/416; 356/311; 250/226
[58] Field of Search ................... 356/315, 317, 356/318, 416, 417, 419, 311; 250/226

[56] References Cited

U.S. PATENT DOCUMENTS

| | | | |
|---|---|---|---|
| 4,306,813 | 12/1981 | Sick ............................... | 356/431 |
| 4,469,441 | 9/1984 | Bernier et al. ................ | 356/316 |
| 4,609,810 | 9/1986 | O'Brien et al. ............... | 356/316 |
| 4,616,137 | 10/1986 | Goff et al. ..................... | 356/417 |
| 4,636,074 | 1/1987 | Levy et al. .................... | 356/328 |
| 4,776,702 | 10/1988 | Yamaba ......................... | 356/419 |
| 4,859,277 | 8/1989 | Barna et al. ................... | 156/626 |
| 5,108,932 | 4/1992 | Wolfbeis ....................... | 356/417 |
| 5,185,265 | 2/1993 | Steen et al. ................... | 356/417 |
| 5,288,367 | 2/1994 | Angell et al. ................. | 156/626 |
| 5,308,414 | 5/1994 | O'Neill et al. ................ | 156/626 |
| 5,537,247 | 7/1996 | Xiao .............................. | 359/368 |
| 5,656,807 | 8/1997 | Packard ......................... | 250/214 |

FOREIGN PATENT DOCUMENTS

| | | | |
|---|---|---|---|
| 0 571 760 A1 | 12/1993 | European Pat. Off. ......... | G02F 1/23 |
| 1 595 587 | 2/1977 | United Kingdom ............. | G01S 3/78 |
| 2 014 752 | 1/1979 | United Kingdom ........... | G02B 27/14 |
| WO 94/04893 | 3/1994 | WIPO .............................. | G01J 3/12 |

*Primary Examiner*—Robert H. Kim
*Assistant Examiner*—Zandra Smith
*Attorney, Agent, or Firm*—Thosason, Moser, Patterson

[57] ABSTRACT

Apparatus for bandpass photon detection containing a lens for collimating input light, a bandpass filter element, and a photomultiplier detector. Light passes from a source into the lens which collimates the light which then is incident upon the filter. The filter is tuned to a particular band of wavelengths, such that out of all of the wavelengths that are incident upon the front side of the filter, a wavelength band is propagated through the filter and passes from the filter to the photomultiplier detector, such that the output of the photomultiplier detector is a voltage level representing the energy content within that wavelength band. In various alternative embodiments, the bandpass photon detectors are arranged in a number of cascade arrangements such that multiple wavelength bands are simultaneously detected.

12 Claims, 5 Drawing Sheets

BANDPASS PHOTON DETECTOR

BACKGROUND OF THE DISCLOSURE

1. Field of the Invention

The invention relates to apparatus for performing optical emission spectroscopy and, more particularly, to apparatus for performing optical emission spectroscopy to analyze plasma enhanced processes. Within a semiconductor wafer processing system

2. Description of the Background Art

Optical emission spectroscopy has been used in the prior art for monitoring and analyzing the characteristics of a plasma within a dry etch reaction chamber of a semiconductor wafer processing system. Optical emission spectroscopy (OES) is accomplished using a monochromator that is coupled to a transparent viewing window of the reaction chamber. Light generated by the plasma is carried by an optical fiber to the monochromator, and the monochromator selects a particular wavelength for analysis using a diffraction grating. The particular wavelength is disbursed from the grating at a specific angle to a photomultiplier detector or some other form of light detector. The photomultiplier detector (PMD) or other form of photo detector produces an electrical voltage representing the magnitude of energy at the particular wavelength selected by the monochromator. This voltage is typically analyzed by a computer system to detect and/or control the end point of a plasma enhanced etch process. Such OES systems have many uses in analyzing, characterizing and otherwise monitoring a plasma within a reaction chamber of a semiconductor processing system. Such OES systems are disclosed in U.S. Pat. Nos. 5,288,367 issued Feb. 22, 1994; 5,308,414 issued May 3, 1994; and 4,859,277 issued Aug. 22, 1989.

Typically, the monochromator selects a wavelength from the broad spectrum optical signal produced by the plasma using a diffraction grating. Such a defraction grating is inefficient in its selection process and significantly degrades the magnitude of the selected wavelength. Consequently, the monochromator of this sort is inefficient and the number of photons that arrive on the photo sensitive area of the detector is significantly less than the number actually available for detection, resulting in high shot noise content within the detected signal.

Therefore, there is a need in the art for a more efficient optical signal detector that may efficiently select and analyze a band of wavelengths from the broadband optical signal generated by a plasma within a reaction chamber of a plasma enhanced semiconductor wafer processing system.

SUMMARY OF THE INVENTION

The present invention overcomes the disadvantages heretofore associated with the prior art by monitoring a plasma within a reaction chamber of a semiconductor processing system using a bandpass photon detector that does not use a grating to select a wavelength for detection. Specifically, the detector of the present invention is coupled to a transparent window of the reaction chamber via a fiber optic cable. The bandpass photon detector contains a lens for collimating the light propagating within the fiber optic cable, a bandpass filter element, and a light detector such as a photomultiplier detector.

In operation, light passes from the fiber optic cable into the lens which collimates the light. The collimated light is incident upon the filter element. The filter element is tuned to a particular wavelength band of the light. As such, out of all of the wavelengths that are incident upon the front side of the filter element, a particular band of wavelengths is propagated through the filter element. The selected wavelengths pass from the filter element to the photomultiplier detector such that the output of the photomultiplier detector is a voltage level representing the energy content within the selected band of wavelengths.

To detect multiple bands of wavelengths, a plurality of bandpass photon detectors can be cascaded. In the simplest cascade form, the optical fiber that couples light from the chamber to the invention is split, and each of the split cable ends is connected to a respective bandpass photon detector. The filter elements in each of the bandpass photon detectors are tuned to a different wavelength band, such that the output voltage of each photomultiplier detector represents the magnitude of the energy at the particular wavelength band detected by each bandpass photon detector in the cascade arrangement. Consequently, the invention provides simultaneous measurement and analysis of multiple wavelength bands of light emissions. However, since this embodiment distributes the light to the detectors by splitting the fiberoptic cable, such a configuration reduces the light intensity (I) by I/N, where N is the number of wavelengths that are detected.

Alternatively, the bandpass photon detectors may be cascaded such that one bandpass photon detector extracts a particular wavelength band to analyze and reflects the remaining light energy to the next bandpass photon detector in the cascade, and so on, until a plurality of wavelength bands have been extracted for analysis. Specifically, the filter element in each bandpass photon detector of the cascade network are angled at less than 50°, such that a particular wavelength band of light is passed through the angled filter element to a first photomultiplier detector. The remaining light is reflected from the first filter element to a second filter element also positioned at a predefined angle relative to the incident light. A second wavelength band is passed through the second filter element to a second photomultiplier detector. The remaining light is then reflected to a third filter element where a third wavelength band is transmitted through the third filter and measured by a third photomultiplier detector, and so on. Each filter is greater than 80% reflective, such that a relatively large number of filters may be cascaded to simultaneously measure a series of wavelength bands.

Additionally, the bandpass photon detectors can be arranged in varied geometries such as a star pattern, a linear array having a filter/distributor array to channel optical signals to each bandpass photon detector, and the like. The bandpass photon detector provides a high sensitivity measurement device for measuring light at selected wavelengths over a large solid angle. The bandpass photon detector cascade arrangement achieves very high sensitivity, spectrally resolved, optical emission detection that simultaneously detects light at a variety of wavelengths. Such an arrangement does not degrade spectral resolution or optical signal sensitivity during the measurement process. The bandpass photon detector, either singly or in a cascade arrangement, finds use in any application where high sensitivity measurement of selected wavelength bands is desired. The invention is particularly useful in optical emission spectroscopy (OES) systems used to monitor and characterize a plasma within a plasma enhanced semiconductor wafer processing system.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
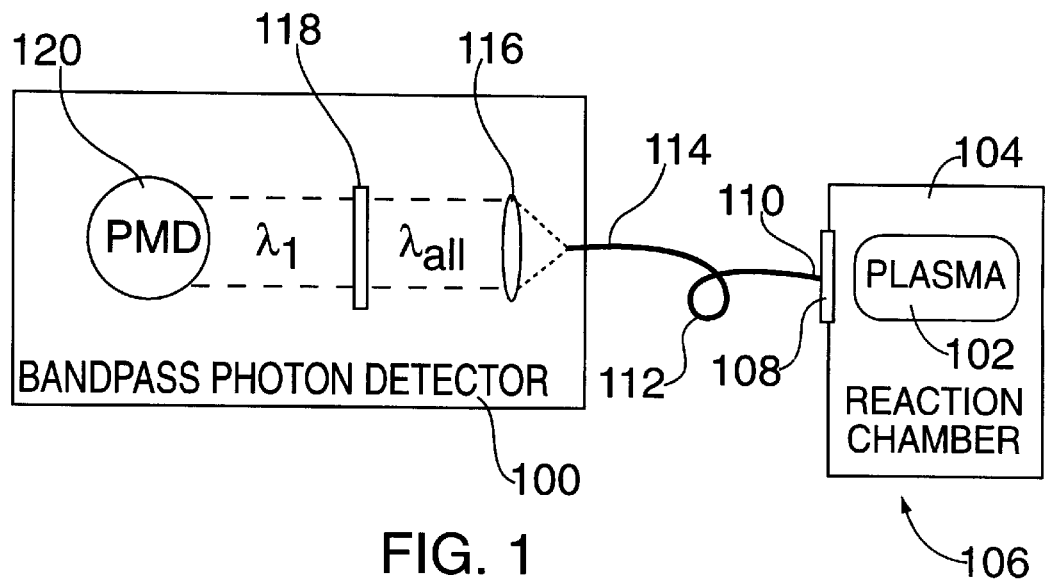
FIG. 1 depicts a bandpass photon detector in accordance with the present invention.

The present invention is a bandpass photon detector 100 for monitoring optical emission characteristics of a plasma 102 within a reaction chamber 104 of a plasma enhanced semiconductor wafer processing system 106. The present invention is also applicable to any art wherein a plasma or other light emitting phenomenon requires monitoring. As such, the plasma and plasma source should be considered an illustrative light source for the invention.

The bandpass photon detector 100 of the present invention is attached to the reaction chamber 102 via a coupling port 108. The light emitted by the plasma 102 is coupled to one end of a fiber optic cable 112 that is connected to port 108, and the second end of the fiber optic cable is connected to the detector 100 of the present invention. Specifically, the first end 110 of the fiber optic cable is coupled to a transparent access window 108 of the reaction chamber. The fiber optic cable 112 is comprised of a plurality of individual fibers forming a fiber bundle. One illustrative fiber bundle contains 240 individual fibers, where each fiber has a 220 $\mu$m diameter forming a numerical aperture of 0.4 for the cable. AS the light exits the second end 114 of the fiber optic cable 112, the light diverges at up to approximately a 23° angle.

To collimate the diverging light, the detector 100 contains a lens 116 that collimates the light as it exits the fiber optic cable 112. The distance between the second end 114 of the fiber optic cable 112 and the lens 116 is such that the light beam exiting the lens is approximately a parallel beam.

The bandpass photon detector 100 also contains a filter element 118 that is tuned to transmit a particular band of wavelengths of light and reflect all others, e.g., the filter is an optical bandpass filter. The transmitted wavelength band is coupled to an optical detector such as a photomultiplier detector (PMD) which detects the energy of the light and converts the photons therein into a voltage level. As such, the output of the photomultiplier detector represents the energy at the particular wavelength band passed by the filter.

Illustratively, to select and measure a band of wavelengths, for example, Co emission band centered at 483.5 nm with FWHM (Full Width and Half Maximum) of 2 nm, the filter element is manufactured by Omega Optics under model number 483.5NB2.0, and the photomultiplier detector is manufactured by Hamamatsu of Japan under model number R928.

The bandpass photon detector of the present invention provides a compact, efficient apparatus for use in all plasma monitoring applications. Because of its compact size, the bandpass photon detector can be attached directly to the window of a reaction chamber containing the plasma. As such, a fiber optic cable may not be necessary.

Figure 2:
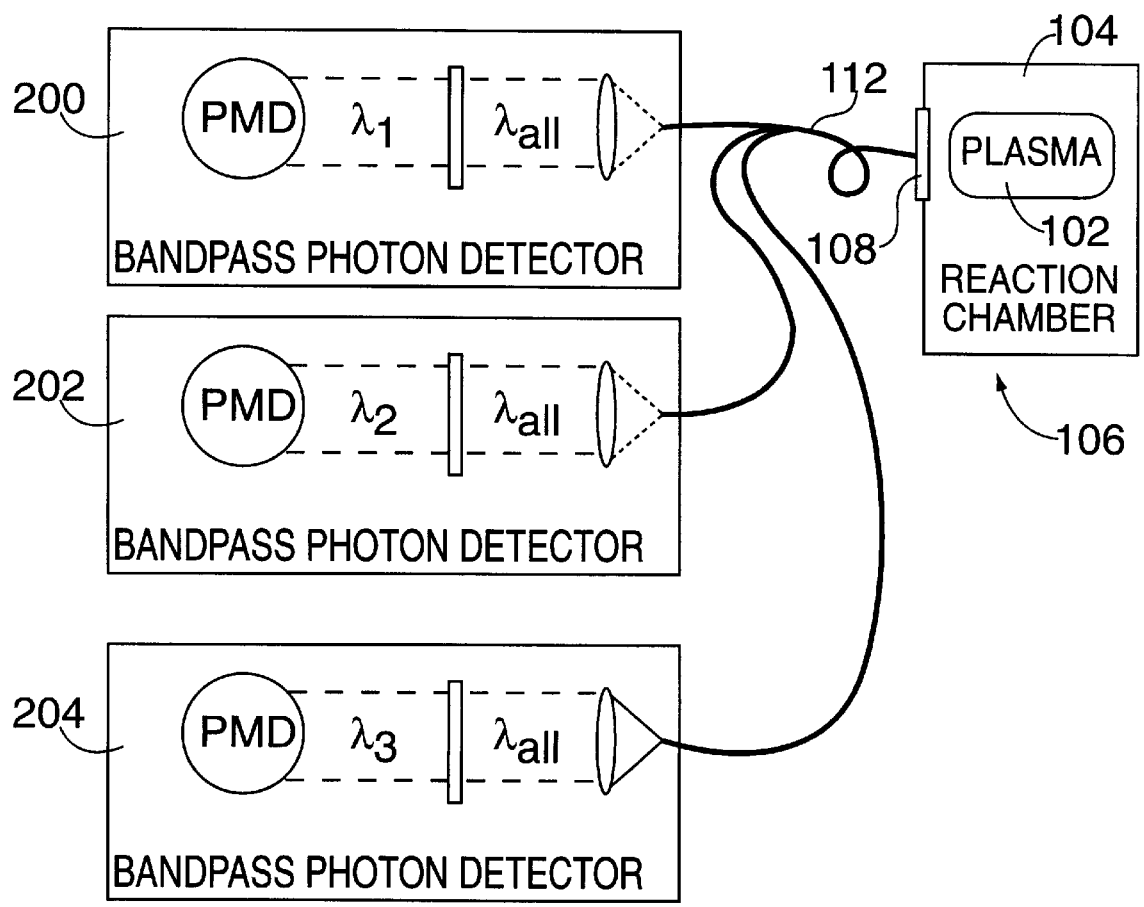
FIG. 2 depicts a cascade arrangement of bandpass photon detectors using a split optical fiber to distribute optical signals to a plurality of the detectors.

FIG. 2 depicts the bandpass photon detector of FIG. 1 arranged in a cascade, split fiber arrangement. The split fiber arrangement contains a plurality of bandpass photon detectors 200, 202 and 204 of the present invention having filter elements that are tuned to different wavelength bands, e.g., $\lambda_1$, $\lambda_2$ and $\lambda_3$. The input fiber 112 is split by dividing the number of individual fibers (e.g., 240 fibers) by N, where N is the number of cascaded bandpass photon detectors. For example, in the illustrative three bandpass photon detector cascade of FIG. 2, the 240 fibers are divided such that 80 fibers are coupled to each of the bandpass photon detectors 200, 202, 204. If additional wavelength bands are to be measured, other bandpass photon detectors can be added by further splitting the fiber. In lieu of physically splitting the cable, an energy splitter can be placed within the fiber to channel the light to each of the bandpass photon detectors.

Figure 3:
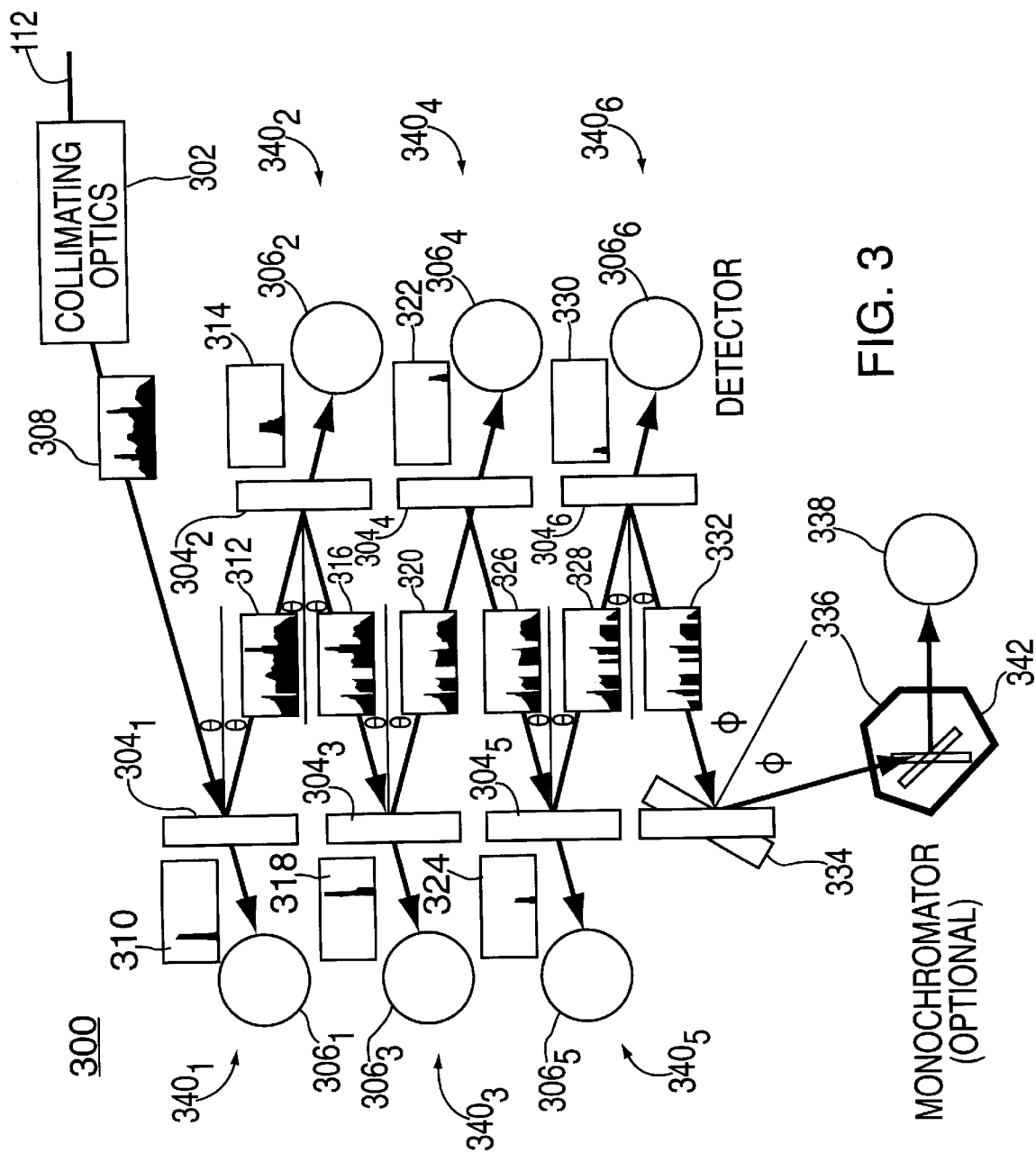
FIG. 3 depicts a cascade arrangement of bandpass photon detectors using a reflective, linear cascade pattern.

FIG. 3 depicts an alternative embodiment of the present invention, an integrated cascade system 300 of bandpass photon detectors $340_n$ (n=1, 2, 3, ... N). In this embodiment, each filter element $304_n$ is angled at an angle approximately 20° relative to the incident light beam, such that incident energy from the input collimating optics 302 is reflected at an angle 2θ from the filter element to another filter element $304_{n+1}$. As such, a cascade of bandpass photon detectors $304_n$ is arranged in a pattern, where each bandpass photon detector $340_n$ measures a particular wavelength band and the remaining wavelengths are passed to subsequent bandpass photon detectors $340_{n+1}$ in the cascade.

More specifically, cascade system 300 contains collimating optics 302, filter elements $304_n$ and detectors $306_n$. The collimating optics 302 collimate light that enters the cascade from a fiber optic cable 112. Each filter element $304_n$ passes a wavelength band to its associated detector (photomultiplier detector (PMD) $306_n$ or other form of photo detector). The cascade of filter elements and PMDs begins with a first filter element $304_1$ and PMD $304_1$. The reflected light energy from filter element $304_1$ is directed to a second filter element $304_2$ which passes a second band of wavelengths to a second PMD $306_2$. This filter element $304_2$ reflects light energy to other filter elements, and so on, such that the cascade bandpass photon detectors may measure simultaneously any number of wavelength bands of the input light.

To illustrate the wavelength band extraction, FIG. 3 contains a spectral plot before and after each filter element. For example, a full spectrum plot 308 represents the full spectrum of light that is produced by the collimating optics 302. Plot 310 depicts the spectrum passed by the first filter element $304_1$, while plot 312 depicts the spectrum that is reflected from the first filter element $304_1$ e.g., the full plot 308 less the and in plot 310. Plots 314–332 depict the various other transmitted and reflected spectrums. Each filter element is greater than 85% efficient in reflecting and transmitting the energy of interest, such that a substantial number of elements can be cascaded before the signal level is degraded to a point that it cannot be easily detected without substantial signal processing. The cascaded system provides a compact, simultaneous multiband analysis system that allows for processing these light signals with very high sensitivity to improve semiconductor process monitoring such as end point detection of an etch process.

Optionally, the cascade system is terminated with a series arrangement of a fully reflective mirror 334, a monochromator 336 and a PMD 338. Such a termination to the cascade allows for any of the remaining wavelength bands to be selected by the monochromator 336 and detected by the PMD 338. Wavelength selection is accomplished by varying the angle of incidence of the monochromator grating 342 through pivoting the mirror 334, the grating 342, or both. This form of termination provides additional system flexibility.

Figure 4:
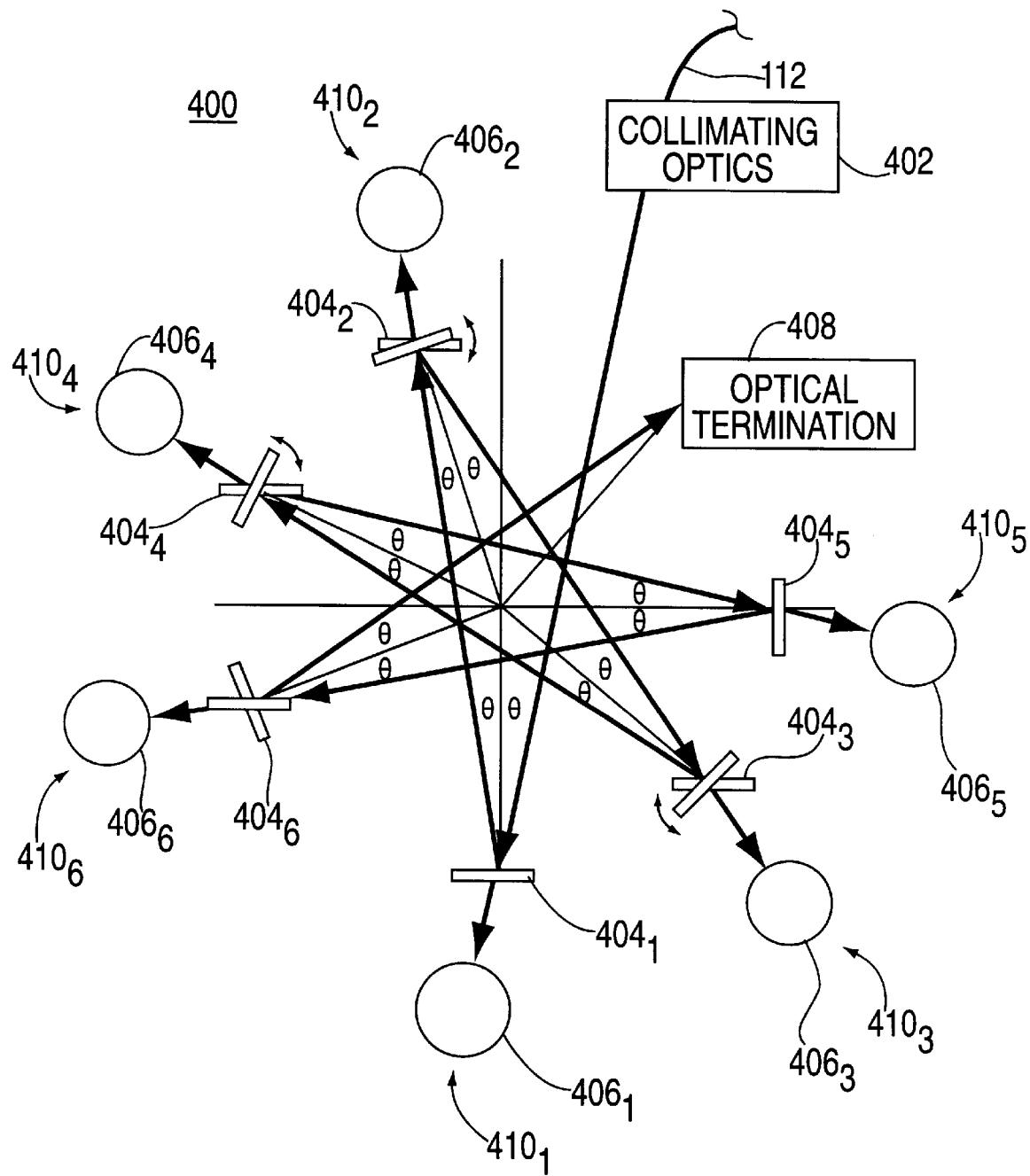
FIG. 4 depicts a cascade arrangement of bandpass photon detectors using a reflective star pattern.

FIG. 4 depicts an alternative embodiment of the cascade system 400 having a star arrangement of bandpass photon detectors $410_n$ (n=1,2,3, . . . N). The system 400 contains collimating optics 402, a plurality of filter elements $404_n$, a plurality of detectors $406_n$ and an optical termination 408. An optical signal is coupled by fiber optic cable 112 to the collimating optics 402 which collimate the optical signal into a beam. The beam is focused upon a first filter element $404_1$. Filter element $404_1$ transmits a particular wavelength band of optical signal to detector $406_1$ such as a photomultiplier detector. The remaining spectrum not selected by filter element $404_1$ is reflected toward filter element $404_2$. A combination of the second filter element $404_2$ and its associated detector $406_2$ forms a second bandpass photon detector $410_2$. The second filter element, in a similar manner to the first filter element, selects a particular wavelength band for detection and reflects the remaining spectrum. The remaining spectrum is focused upon a third filter element within a third bandpass photon detector $410_3$. This wavelength band extraction and reflection technique is repeated for any number of wavelength bands.

To obtain focus of reflected energy from one bandpass photon detector to another, a plurality of the filter elements, e.g., elements $404_2$, $404_3$, and $404_4$, are mechanically pivotable to achieve beam alignment and focus onto subsequent filter elements. Such adjustability is represented by an arrow next to the adjustable filter elements.

In the illustrative star pattern arrangement, the last bandpass photon detector $410_6$ contains filter element $404_6$ and detector $406_6$. The remaining energy reflected from filter element $404_6$ is reflected into an optical termination 408 which absorbs the remaining optical energy. Alternatively, as in system 300 depicted in FIG. 3, the optical termination can be replaced by a collimator and detector combination to selectively detect the remaining optical signal.

Figure 5:
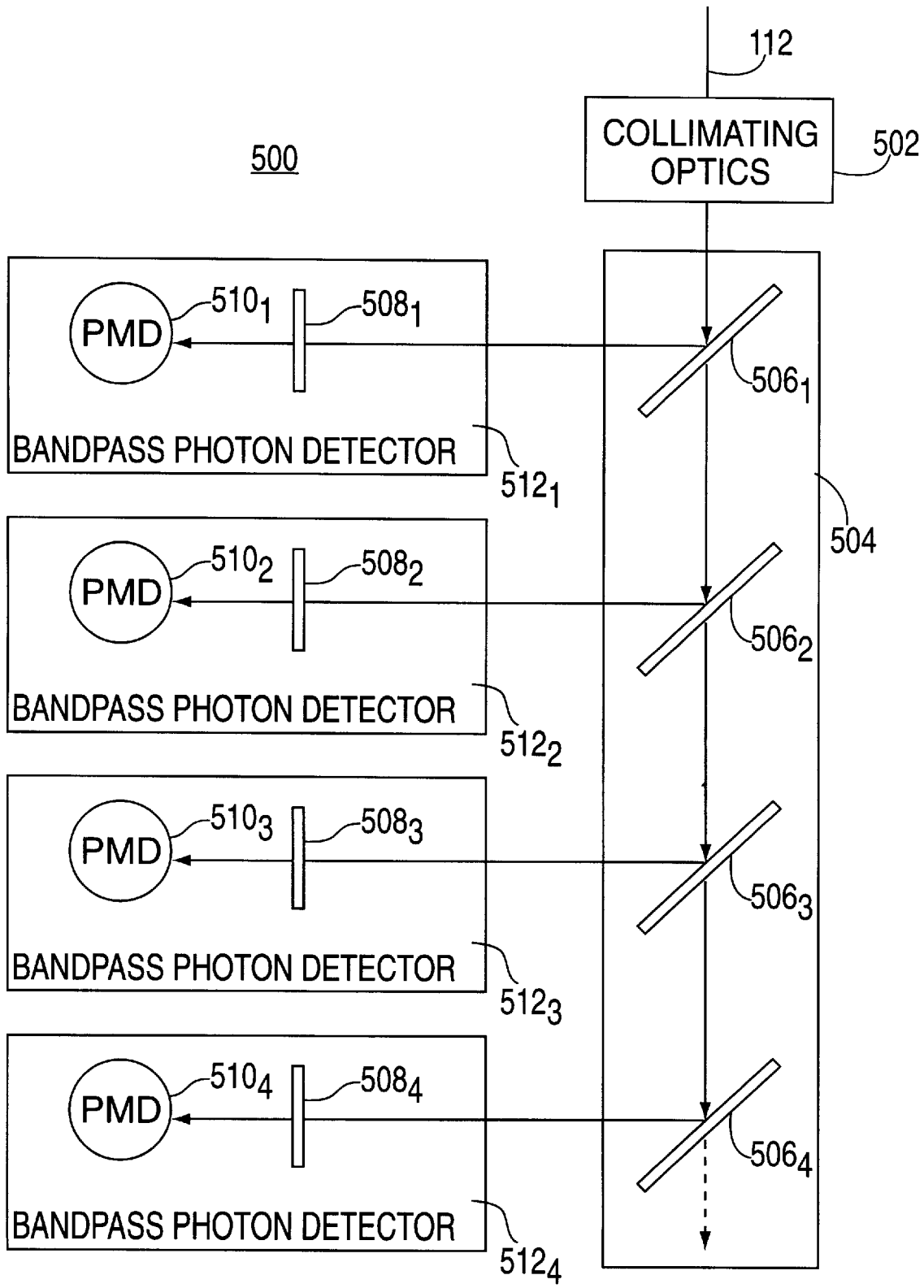
FIG. 5 depicts a cascade arrangement of bandpass photon detectors coupled to a light filter/distributor.

FIG. 5 depicts a second alternative embodiment of a cascade system 500 using a linear arrangement of bandpass detectors $512_n$ (n=1,2,3, . . . N) coupled to a light filter/distributor 504. The system 500 contains an optical signal filter/distributor 504, coupled to a plurality of bandpass filter elements $508_n$ and detectors $510_n$. The optical signal filter/distributor 504 comprises a plurality of lowpass or high pass filter elements $506_n$ aligned in a collinear arrangement such that the incident beam from the collimating optics 502 is focused upon the first filter element $506_1$. The first filter element $506_1$ reflects a portion of the spectrum towards the first bandpass photon detector $512_1$, filter element $508_1$ and detector $510_1$. The remaining spectrum is passed through the filter element $506_1$ to filter element $506_2$ wherein another portion of the spectrum is reflected towards a second bandpass photon detector $512_2$. This process continues until the final filter element $506_4$ reflects the remaining spectrum towards the last bandpass photon detector $512_4$.

The reflected spectrum from each element $506_n$ is generally broader than the bandwidth of energy that is detected in each detector $510_n$ within the bandpass photon detectors $512_n$. To achieve such wavelength selection, the filter elements $506_n$ are low pass or high pass filter elements. The last filter element $506_n$ in the filter distributor 504 may be a conventional mirror rather than a filter element.

Figure 6:
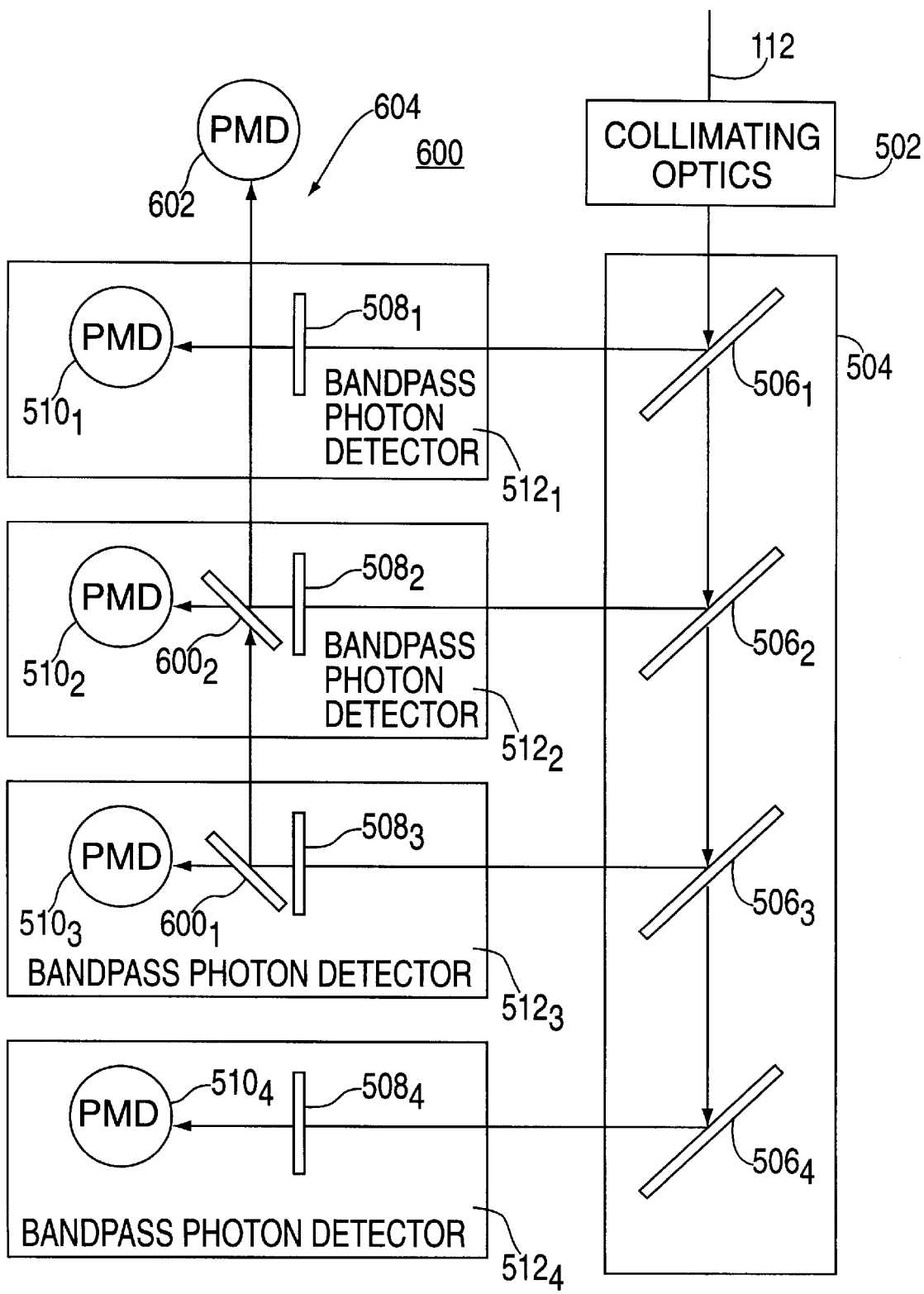
FIG. 6 depicts the arrangement of FIG. 5 further containing a broadband bandpass photon detector.

FIG. 6 depicts a third alternative embodiment of the cascade system 600 that is a modified version of the system 500 depicted in FIG. 5 further containing a combined spectrum analyzer 604. Similar to system 500, system 600 contains collimating optics 502, a filter distributor 504, and a plurality of bandpass photon detectors $512_n$ containing a combination bandpass filter $508_n$ and detector $510_n$. The modification incorporates two low pass or high pass filter elements $600_1$, and $600_2$ within the bandpass photon detectors $512_2$ and $512_3$. The low pass or high pass filter elements $600_1$ and $600_2$ are respectively positioned between the bandpass filter elements $508_1$ and $508_3$, and the detectors $510_2$ and $510_3$. The low pass or high pass filter elements couple selected energy from the bandpass filter outputs to detector 602 such that the detector receives multiple bands of spectrum energy. As such, by positioning various low pass filter elements, such as those depicted in $600_1$ and $600_2$ within the bandpass photon detectors, the system can be made very flexible as far as combining the separate wavelength bands that are analyzed by the system.

The bandpass photon detector arrangement, as well as the various systems that it can be arranged into, provide an ability to deliver the maximum optical signal strength available to each filter element and detector independent of the number of detectors. Such an arrangement allows for a very compact package containing a plurality of detectors within a single scientific instrument. Furthermore, this system allows for flexibility as well as an ability to utilize different filter elements and detectors in various combinations within a single package. Also, the bandpass photon detectors which comprise each of the systems is modular, to be removed and replaced with others, such that varying measurement requirements can be quickly accommodated. As such, system customization is simple and easily achieved. Such a system provides for high spectral resolution as well as detecting a large solid angle of emission volume in conjunction with a multi-channel signal acquisition system such that various spectral bands can be simultaneously measured and/or combined to be detected individually or together.

Although various embodiments which incorporate the teachings of the present invention have been shown and described in detail herein, those skilled in the art can readily devise many other varied embodiments that still incorporate these teachings.

What is claimed is:

1. A system for measuring a plurality of bands of wavelengths of an optical signal, said system comprising:
   a plurality of bandpass photon detectors, arranged in a cascade pattern, for detecting respectively different bands of wavelengths, where each bandpass photon detector comprises:
   a filter element for transmitting a predefined band of wavelengths of the optical signal and reflecting other predefined wavelengths of the optical signal; and
   an optical signal detector, optically coupled directly to said filter element, for generating a voltage that represents the energy in the predefined band of wavelengths that is transmitted by the filter element;
   where at least one of said filter elements is aligned to transmit a predefined band of wavelengths of the optical signal directly to an optical signal detector and reflect other predefined wavelengths of the optical signal to at least one other of the bandpass photon detectors; and
   a monochromator detector, coupled to a last bandpass photon detector in said cascade pattern, for selecting a band of wavelengths from a remaining optical signal for detection.

2. The system of claim 1 further comprising a spectrum analyzer, coupled to selected ones of said plurality of bandpass photon detectors, for combining and analyzing a plurality of the predefined bands of wavelength.

3. The system of claim 1 wherein the cascade pattern of bandpass photon detectors is formed by positioning a plurality of bandpass photon detectors equidistant from a central point and having each of the filter elements in the bandpass photon detectors substantially facing the central point.

4. The system of claim 1 wherein each of said filter elements has a surface and the optical signal has an angle of incidence upon the surface of the filter element to cause said predefined band of wavelengths of the optical signal to propagate through said filter element and cause said other predefined band of wavelengths of the optical signal to be reflected toward said other bandpass photon detector.

5. The system of claim 1 wherein the plurality of bandpass photon detectors comprises N bandpass photon detectors, where N is an integer, and each of the N bandpass photon detectors is arranged in said cascade pattern to cause a reflected optical signal to be incident upon another one of the bandpass photon detectors or a termination.

6. The system of claim 1 wherein said predefined band of wavelengths has a bandwidth of approximately 2 nm.

7. A system for measuring a plurality of bands of wavelengths of an optical signal, said system comprising:

a plurality of bandpass photon detectors, arranged in a cascade pattern formed by positioning the plurality of bandpass photon detectors equidistant from a central point and having each of the bandpass photon detectors substantially facing the central point and aligned to cause a reflected optical signal to be incident upon another one of the bandpass photon detectors or a termination, where each of the bandpass photon detectors measures a predefined band of wavelengths of the optical signal and reflects other bands of wavelengths of the optical signal.

8. The system of claim 7 wherein each of the bandpass photon detectors comprises:

a filter element for transmitting said predefined band of wavelengths of the optical signal and reflecting said other predefined wavelengths of the optical signal; and an optical signal detector, optically coupled to said filter element, for generating a voltage that represents the energy in the predefined band of wavelengths that is transmitted by the filter element.

9. A system for measuring a plurality of bands of wavelengths of an optical signal produced by a plasma within a semiconductor wafer processing chamber, said system comprising:

a plurality of bandpass photon detectors for detecting a respectively different bands of wavelengths, where each bandpass photon detector comprises:

a first filter element for transmitting a predefined band of wavelengths of the optical signal and reflecting other predefined wavelengths of the optical signal; and an optical signal detector, optically coupled to said first filter element, for generating a voltage that represents the energy in the predefined band of wavelengths that is transmitted by the first filter element; and an optical signal distributor having a plurality of second filter elements that reflect certain wavelengths of said optical signal and transmit certain wavelengths of said optical signal, where said second filter elements are arranged in series and each second filter element is associated with a bandpass photon detector that is aligned with said associated second filter element to receive an optical signal that is reflected from said associated second filter element.

10. The system of claim 9 wherein said second filter elements are a plurality of low pass filter elements.

11. The system of claim 9 wherein said second filter elements are a plurality of high pass filter elements.

12. The system of claim 9 further comprising a spectrum analyzer, coupled to selected ones of said plurality of bandpass photon detectors, for combining and analyzing a plurality of the predefined bands of wavelength.

* * * * *